United States Patent [19]

Zurbrügg

[11] Patent Number: 5,755,659
[45] Date of Patent: May 26, 1998

[54] METHOD OF MAKING A VASCULAR PROSTHESIS

[76] Inventor: Heinz Robert Zurbrügg. Bündackerstrasse 158, CH-3047 Bremgarten, Switzerland

[21] Appl. No.: 815,478

[22] Filed: Mar. 11, 1997

Related U.S. Application Data

[62] Division of Ser. No. 346,151, Nov. 29, 1994, Pat. No. 5,645,581.

[30] Foreign Application Priority Data

Nov. 30, 1993 [DE] Germany ............... 43 40 755.2

[51] Int. Cl.⁶ .................. A61F 2/04; A61F 2/06
[52] U.S. Cl. ........................................ 600/36; 623/1
[58] Field of Search .................. 623/1, 11, 12, 623/13; 600/36; 606/151–158; 604/8

[56] References Cited

U.S. PATENT DOCUMENTS

| 3,337,673 | 8/1967 | Jeckel ............... 264/324 |
| 3,626,947 | 12/1971 | Sparks ............. 128/334 R |
| 4,441,215 | 4/1984 | Kaster ..................... 3/1.4 |
| 4,475,972 | 10/1984 | Wong ................... 156/167 |
| 4,743,251 | 5/1988 | Barra ..................... 623/1 |
| 4,986,831 | 1/1991 | King et al. ............ 623/1 |
| 5,192,311 | 3/1993 | King et al. ............ 623/1 |

FOREIGN PATENT DOCUMENTS

| 0055250 | 8/1985 | European Pat. Off. ....... A61F 2/06 |
| 0492481 | 1/1992 | European Pat. Off. ....... A61F 2/06 |
| 2556210 | 6/1985 | France ........................ A61F 2/06 |
| 1205743 | 9/1970 | United Kingdom ........ A61M 29/00 |

*Primary Examiner*—Debra S. Brittingham
*Attorney, Agent, or Firm*—Robin, Blecker, Daley and Driscoll

[57] ABSTRACT

The invention concerns a vascular prosthesis for the replacement of blood vessels in the human or animal body, consisting of a section of a replacement blood vessel (3) which has been taken from a human or animal body and a fibro-elastic tube (2) which is drawn over this vascular section, whose intersecting threads (1) which form the tube wind in spiral form around the longitudinal axis of the tube, wherein the fibro-elastic tube (2) is extended pointwise in the longitudinal direction with alteration of the diameter or is compressed and thereby is caused to contact the replacement vessel evenly over its total area.

14 Claims, 8 Drawing Sheets

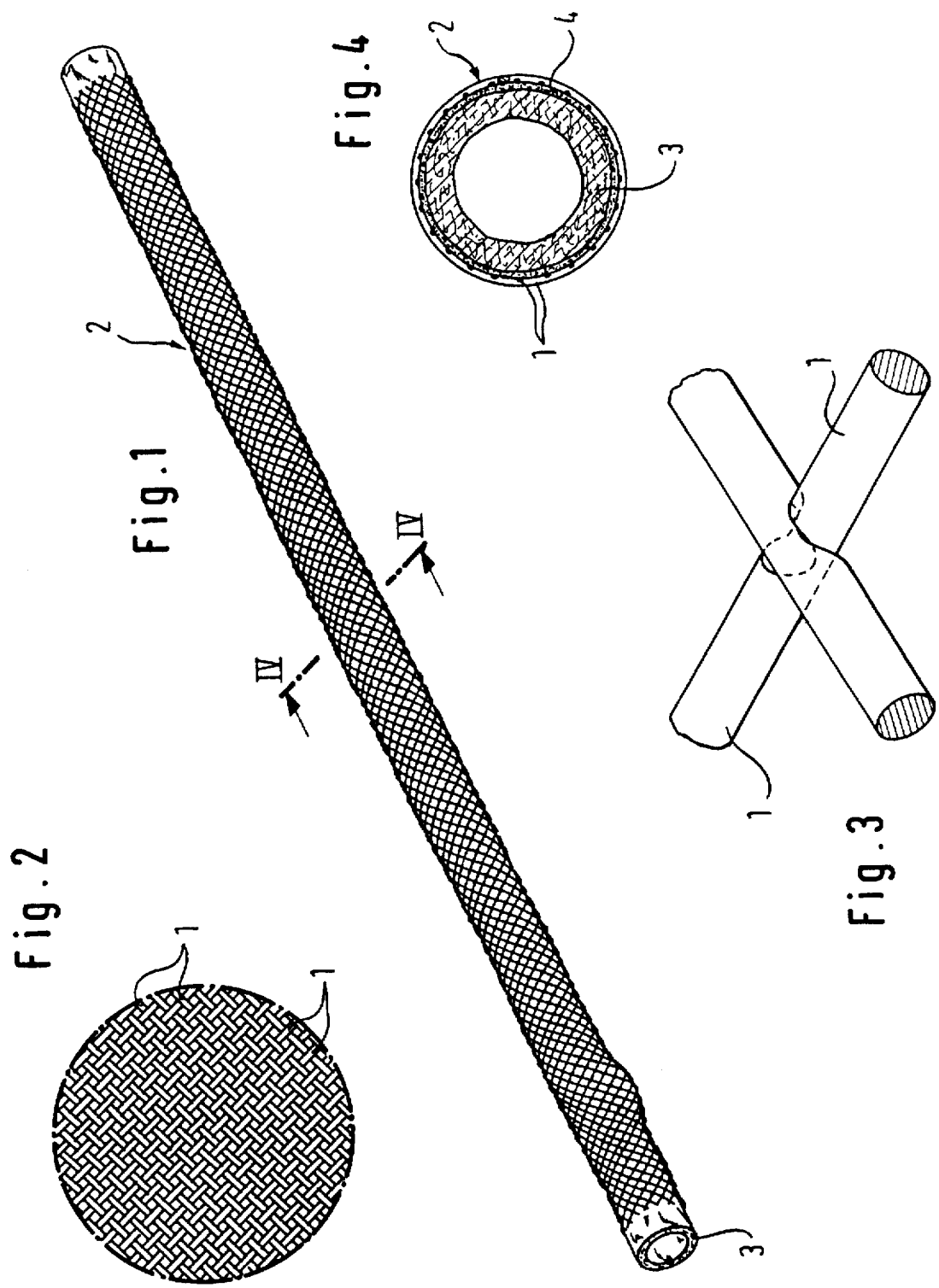

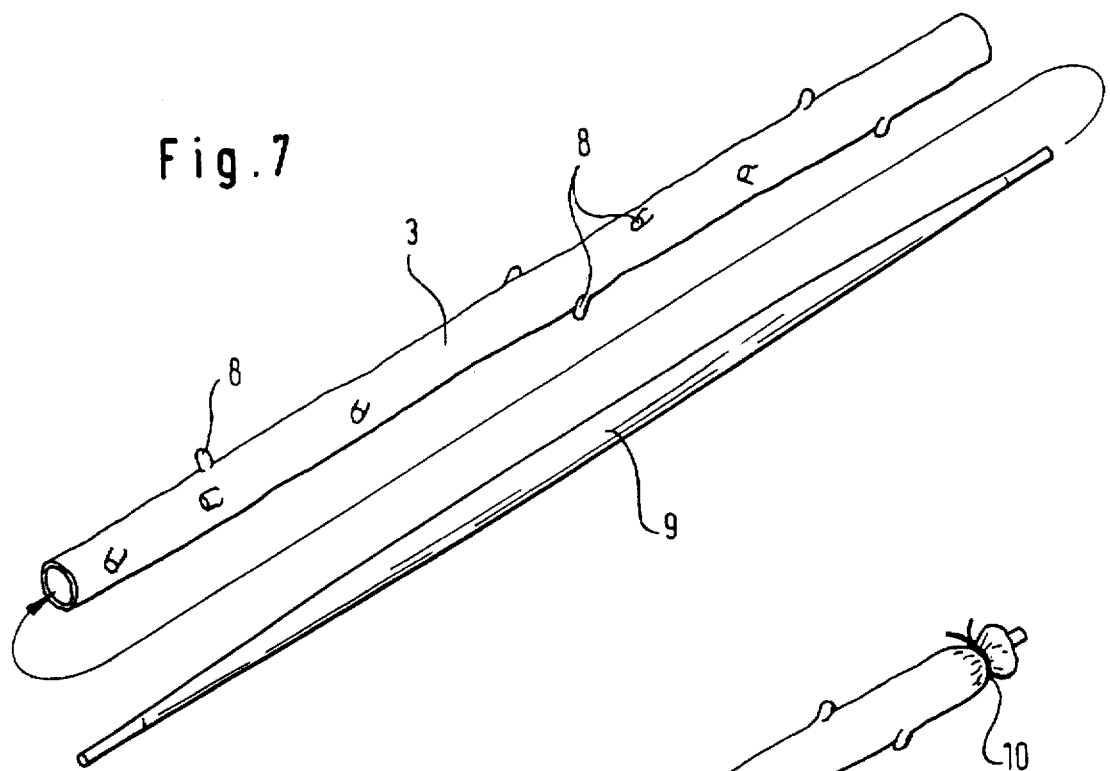
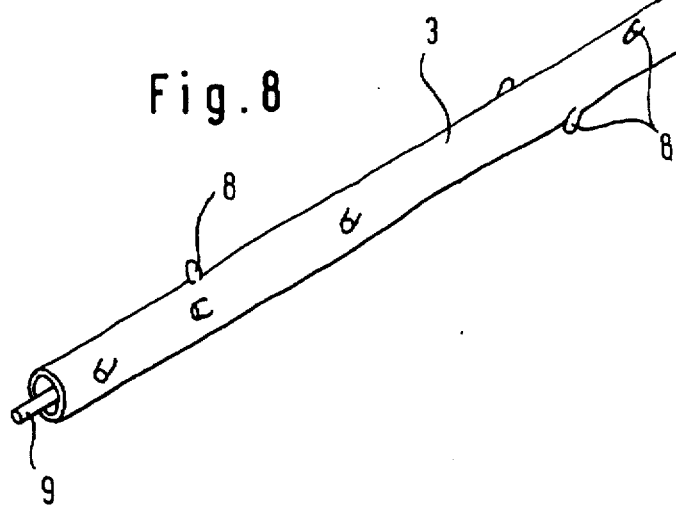

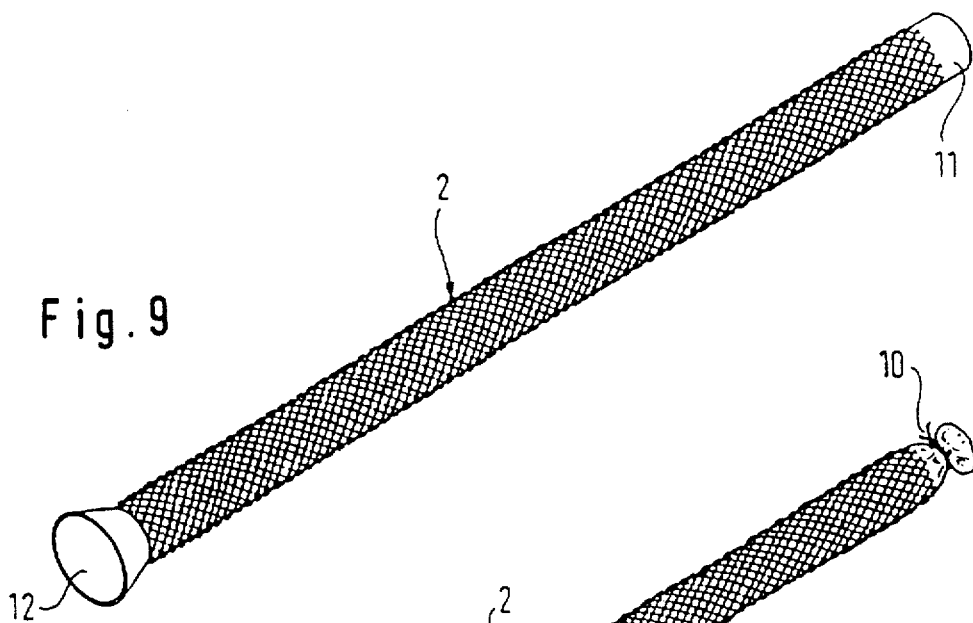
Fig. 9
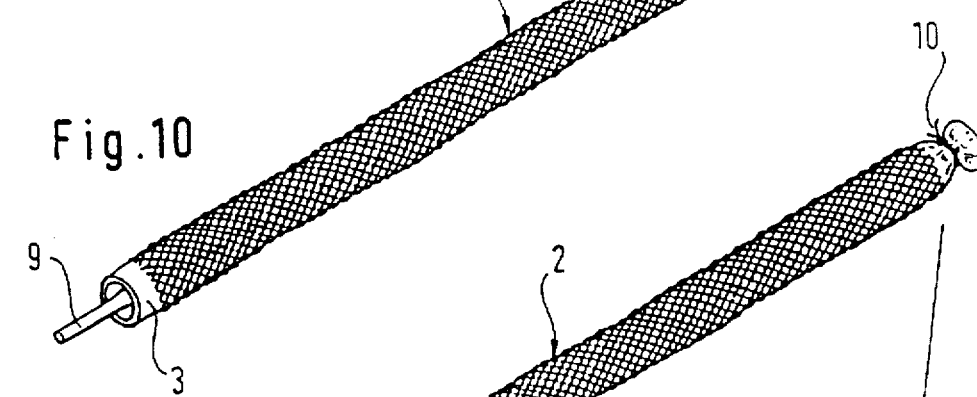
Fig. 10
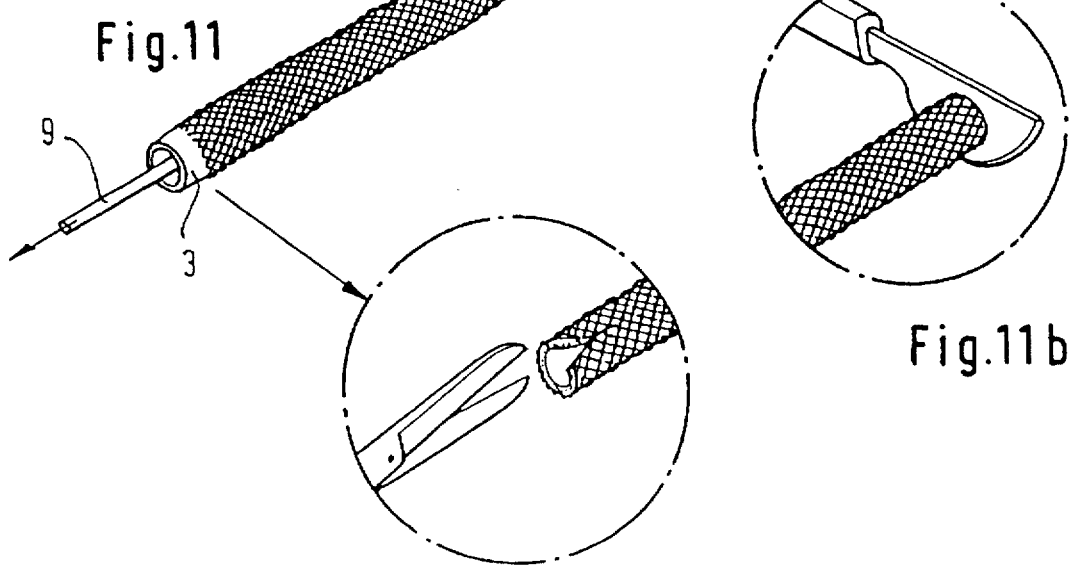
Fig. 11
Fig. 11a
Fig. 11b

METHOD OF MAKING A VASCULAR PROSTHESIS This application is a division of application Ser. No. 08/346,151, filed Nov. 29, 1994, now U.S. Pat. No. 5,645,581.

The invention concerns a vascular prosthesis for the replacement of blood vessels, in particular of arterial blood vessels, in the human or also animal body, which consist of a section of a blood vessel, e.g. a vein, which has been taken from a human or animal body and a fibro-elastic tube (i.e. a tube consisting of flexible thread elements extending spirally and intersecting each other thereby forming a tubular member having a plurality of meshes) which is drawn over this vascular section. Vascular prostheses of this class are already known (e.g. EP-0 055 250 B1). In the case of these prostheses, after the implantation the fibro-elastic tube is also used to support the vascular section on its external side and therefore to avoid an undesirable expansion caused by blood pressure. Furthermore, the invention concerns a process as well as a set of parts for the production of such vascular prostheses.

The known vascular prostheses of the type named initially have fibro-elastic tubes which consist of threads woven together, wherein they have a largely unalterable diameter. Because the replacement blood vessels have a changing, uneven diameter over their length, the known fibro-elastic tubes have the disadvantage that they cannot or can only inadequately be adapted to this different vascular diameter, so that at certain points they do not contact the outer wall of the replacement vessel, and therefore at these points they cannot fulfill the necessary support function for the replacement vessel. Therefore after implantation of the prosthesis in the human body, the result is an undesirable expansion of the replacement vessel at these points and an extension connected therewith accompanied by simultaneous thinning of the vascular wall or there is a scarring at these weak points, which contract the volume of the vessel.

On the other hand, because of the unalterable diameter of the known fibro-elastic tubes there is the danger that the fibro-elastic tube contracts the replacement vessel located in it on the thicker wall points or on the lateral branches of the vessel, whereby the inner diameter of the prosthesis is reduced, which is maximally undesirable from the medical point of view. In addition, in the case of arcuate implantation of the prosthesis, there is the danger of the bending of the prosthesis, which should also be avoided from the medical aspect.

Therefore the invention is based on the object of avoiding this disadvantage of a vascular prosthesis of the class named initially, i.e. of creating a vascular prosthesis of a replacement vascular section which is covered with a fibro-elastic tube, in which the replacement vessel is fully supported over its entire length by the fibro-elastic tube, i.e. in which the fibro-elastic tube also makes contact over its entire length and over the total periphery of the replacement vessel substantially evenly with the irregularly formed outer wall of the vessel to support it, so that a radial extension at certain points of the replacement vessel wall is excluded by the pressure of the blood flowing through the prosthesis or a radial compression inwards of the vessel wall is excluded substantially by the fibro-elastic tube drawn over it, with reduction of the internal diameter of the prosthesis.

This problem is solved in the case of a vascular prosthesis of the class named initially in accordance with claim 1 in that the fibro-elastic tube is stretched or compressed on the replacement vessel at positions in the longitudinal direction with alteration of diameter and thereby it is caused to contact evenly the replacement vessel over the whole of its area. For this purpose, the fibro-elastic tube should preferably be created so that its diameter is reduced by axial extension up to ten times the diameter of the relaxed tube and can be enlarged up to five times the diameter of the relaxed tube by axial compression.

Because of the extension or compression of the fibro-elastic tube in the longitudinal direction, the diameter of the fibro-elastic tube is expanded or contracted in its diameter with reciprocal positioning alteration of the fibro-elastic yarns which are displaceable in relation to each other, i.e. at certain longitudinal positions, whereby it can be caused to contact the entire surface of the replacement vessel evenly. By this total and even, close fitting contact of the fibro-elastic tube on the replacement vessel, a different extension of the wall of the replacement vessel due to the pressure of the blood flowing in the prosthesis which is inserted in the circulation system of the patient is prevented, because the fibro-elastic tube evenly supports the vascular section at all points. In addition, for the same reason, in the case of arcuate implantation, the danger of a fracture of the prosthesis is largely excluded. Moreover at those points at which the vascular wall is particularly thick or where it has lateral branches, radial compression of the vascular wall with a reduction of the inner diameter of the prosthesis is prevented.

The fibro-elastic yarns can have a yarn thickness of 10 to 200 μm, and can consist of metal or of a metal alloy, preferably of stainless steel, but also of biocompatible plastic. They can also have a coating of biocompatible material, e.g. metal or metal alloy. Preferably, the fibro-elastic yarns have a circular cross-section. But the cross-section can also be elliptical, triangular or polygonal, trapeze-shaped or trapezoidal, rhombus-shaped or rhomboid.

Advantageously, the fibro-elastic tube can have 11 to 201 threads, wherein each thread can have individual features. Preferably, the fibro-elastic threads of the fibro-elastic tube are to some extent displaceable against each other. The surface of the threads should be as smooth as possible, i.e. they should not permit the discernment of any pores, which are greater than 0.5 μm, in a magnification by one thousand times using a scanning electron microscope. The surface of the metal threads can be electro-polished.

The diameter of the fibro-elastic threads should vary over their entire length maximally by 15%, and the mesh size of the intersecting threads 1 of the fibro-elastic tube 2 should amount to from 20 to 850000 μm$^2$ in the case of the relaxed fibro-elastic tube, i.e. without external force influence. This mesh size guarantees an optimal support of the replacement vessel.

Expediently, the fibro-elastic tube should be extensible or contractile over its entire length, wherein its elastic resetting force should amount to maximally 30 ponds with extension to double length or with reduction to one half of its length in the relaxed state.

Expediently, the axially oriented angle between the intersecting fibro-elastic threads amounts to between 70° and 170°. In the case of a preferred embodiment, the threads which extend spirally around the axis of the tube in the untensed state of the tube, i.e. before its compression or extension, predominantly at an angle of about 60° to the longitudinal direction of the tube. This makes possible the maximum-possible reciprocal movement of the fibro-elastic threads in the fibro-elastic tube and it ensures that the fibro-elastic tube is maximally stretched or can be compressed at any discretionary point along its length to up to ten times its length or can be compressed to up to one-fifth of its length.

In order to make possible good handling of the prosthesis during implantation, the fibro-elastic tube should preferably be bonded to the blood vessel section by an elastic biological adhesive in the cured state, whereby a biological composite transplant is obtained, which in contrast to the known prostheses is secured against fracture, when its fibro-elastic tube consists of metal threads, and it can also be imaged in the X-ray process without contrast agents.

The invention also concerns a process for the production of a vascular prosthesis of the type described above in accordance with the invention. This process is characterized in that over the replacement vessel section which has been taken from the human or animal body, a fibro-elastic tube which contacts substantially the outer periphery of the vascular section is drawn, which is displaced on the vascular section over its entire length or in individual longitudinal sections with alteration of the diameter in the longitudinal direction in such a manner that it contacts evenly the outer periphery of the vascular section over its total area by means of its inner diameter, on which an adhesive which is used for the adhesion of the vascular section to the fibro-elastic tube is applied to the fibro-elastic tube and through the fibro-elastic tube on to the vascular section, e.g. by dabbing and/or spraying, and in that then the vascular section is pressed on to the fibro-elastic tube by the application of internal pressure and this pressure is maintained over a period which is sufficiently long for the necessary firm adhesion of the fibro-elastic tube to the vascular section. The adhesive can also be applied before the fibro-elastic tube is moved over the vascular section. The inner pressure can be generated by the introduction of a gaseous or liquid pressure means, e.g. a sterile common salt solution or by the introduction of an expansible rod-shaped balloon into the vascular section from its distal end, which is pressed on to the fibro-elastic tube by filling it with a liquid or gaseous pressure agent, e.g. sterile common salt solution or air, and then it is extracted again after being emptied from the section of the vein which is covered with the fibro-elastic tube.

The invention also concerns a set of parts for the production of the vascular prosthesis in accordance with the invention or for the implentation of the process according to the invention. This set consists of a fibro-elastic tube with alterable diameter due to axial expansion or compression having reciprocally displaceable intersecting fibro-elastic threads, of a tubular guide means for placing the fibro-elastic tube over the replacement vessel and of an expansion member which can be introduced into the replacement vessel to expand and press the replacement vessel on to the fibro-elastic tube.

The inventive vascular prosthesis can be used to replace any blood vessel in human or animal bodies. This prosthesis may by of particular significance for the production of aorta-coronary bypasses.

The drawing shows embodiments of the prosthesis in accordance with the invention as well as embodiments of the process for the production of such a prosthesis and the necessary ancillary means, which will be described in more detail below:

FIG. 1 shows a first embodiment of the inventive vascular prosthesis in inclined view;

FIG. 2 shows a plan view of a cut out from the fibro-elastic tube of this vascular prosthesis in magnified form;

FIG. 3 shows an intersection of two fibro-elastic threads in inclined view in a strongly magnified form;

FIG. 4 is a cross-section through the vascular prosthesis along the line IV—IV in FIG. 1;

FIG. 7 shows an embodiment of the balloon rod before its introduction into a segment of a replacement vessel in inclined view;

FIG. 8 shows the replacement vessel with the balloon rod introduced and secured in an inclined view;

FIG. 9 shows an embodiment of a fibro-elastic tube drawn over a guide tube in inclined view;

FIG. 10 shows the fibro-elastic tube drawn on the guide tube after its postioning over the replacement blood vessel with the inserted balloon rod in the inclined view;

Figure 12:
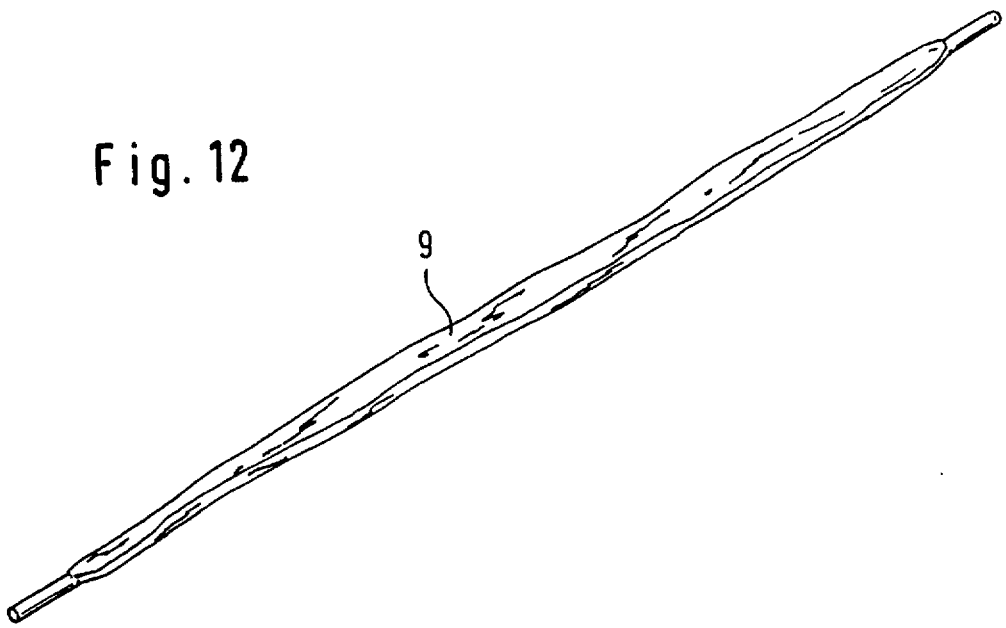
Figure 13:
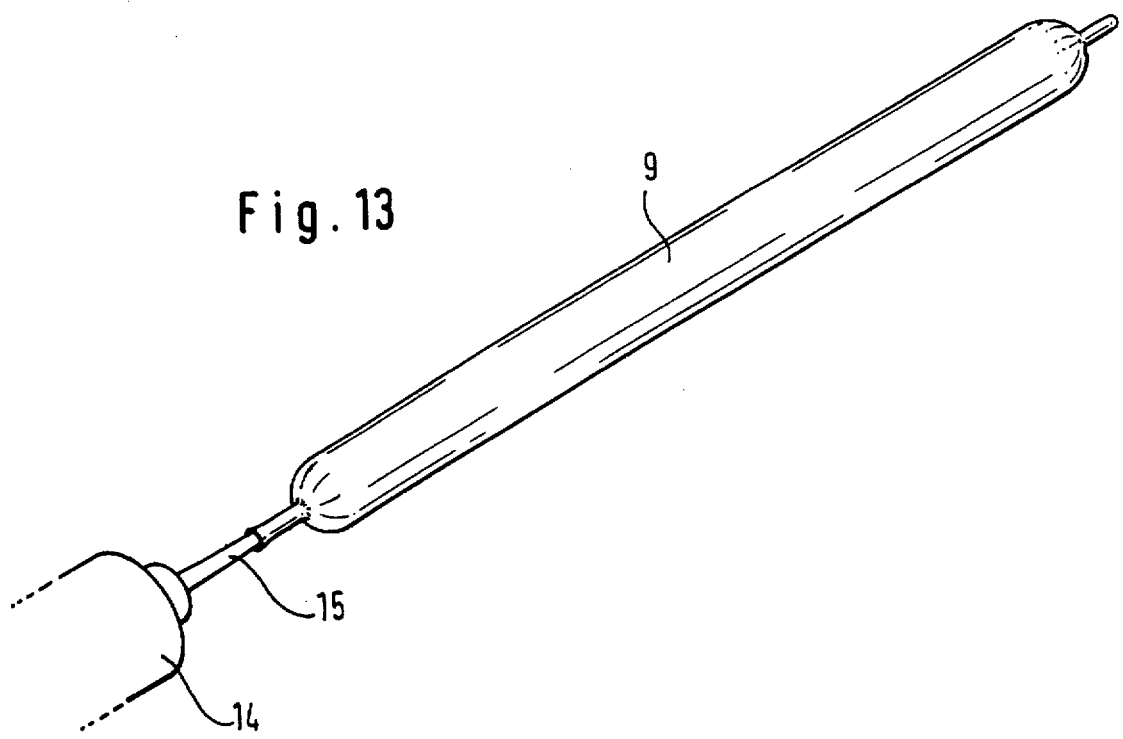
Figure 14:
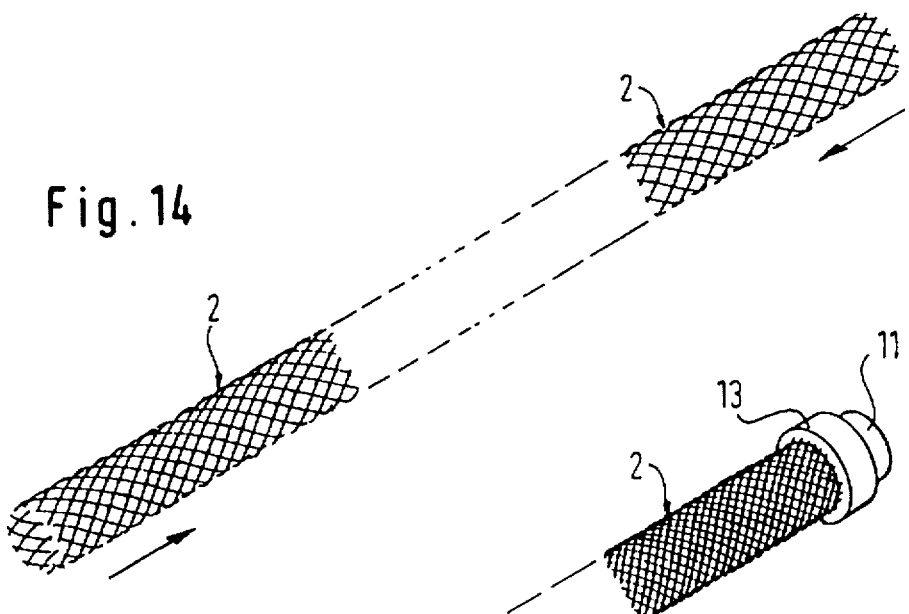
Figure 15:
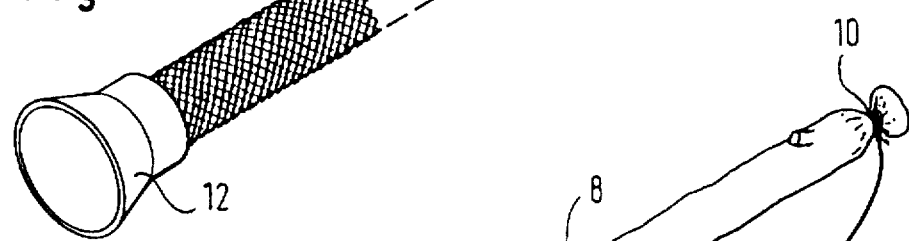
Figure 16:
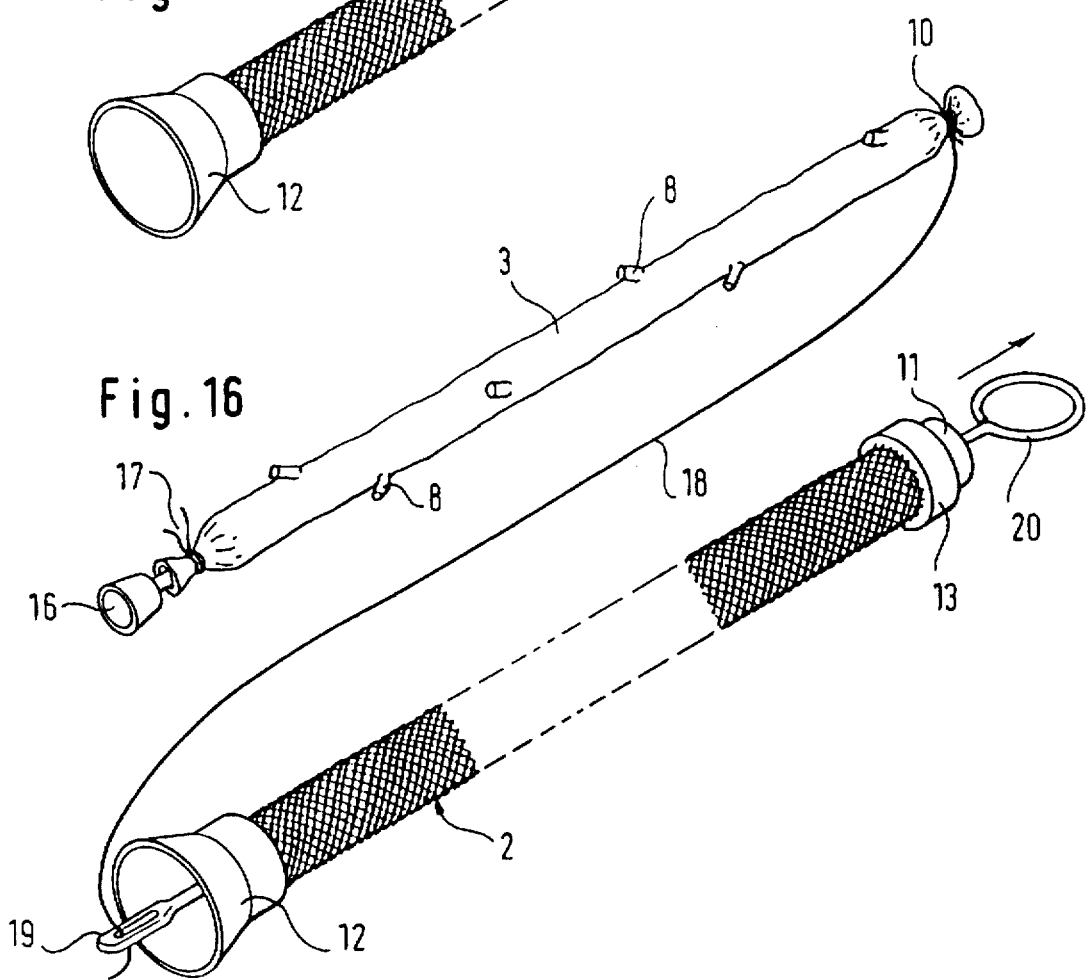
Figure 17:
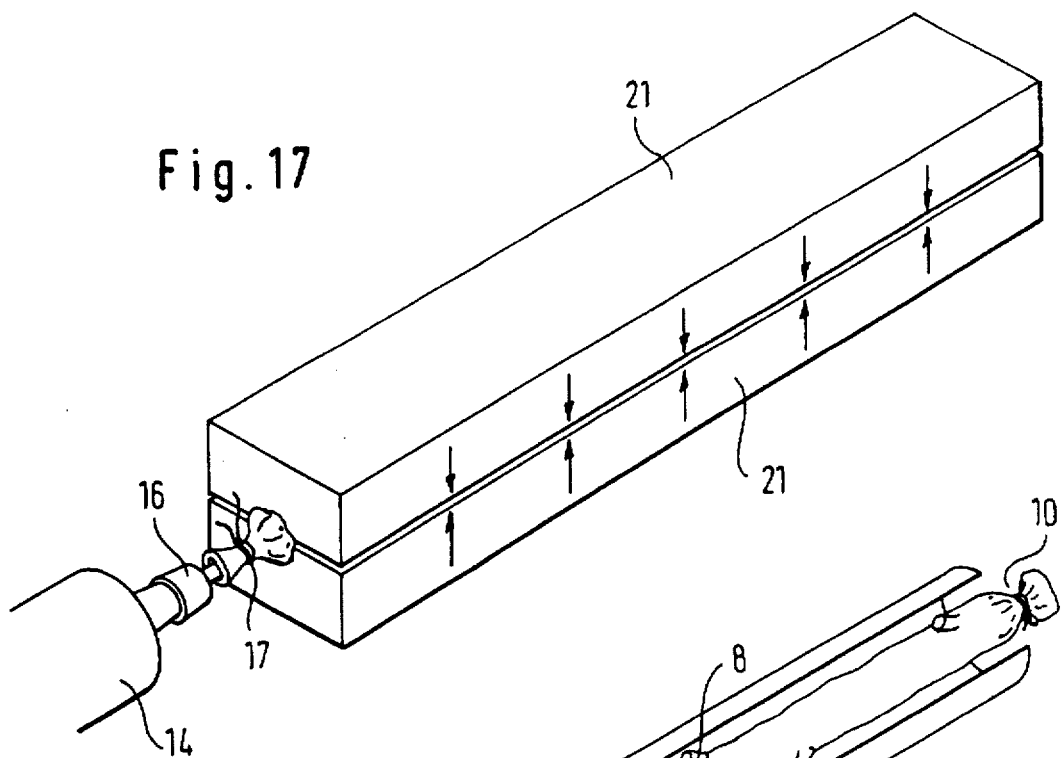
Figure 18:
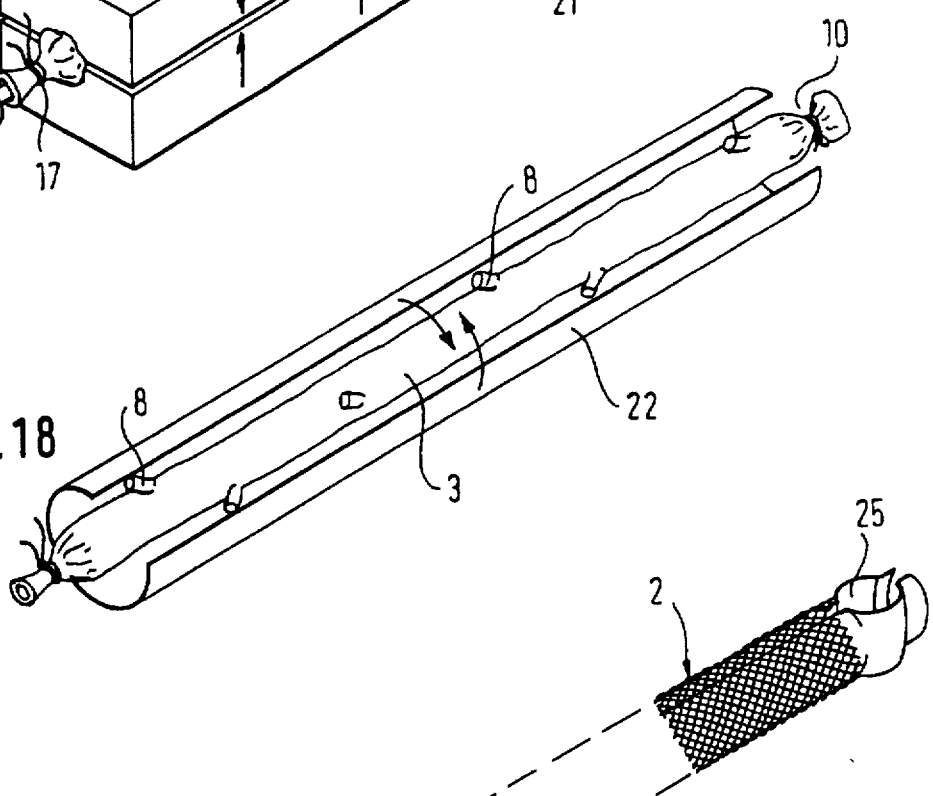
Figure 19:
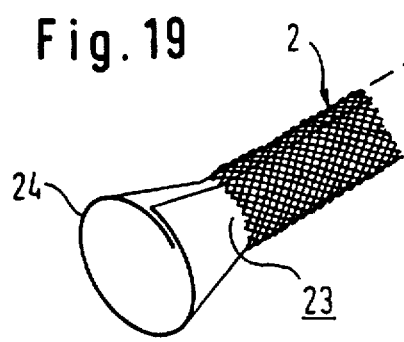
Figure 20:
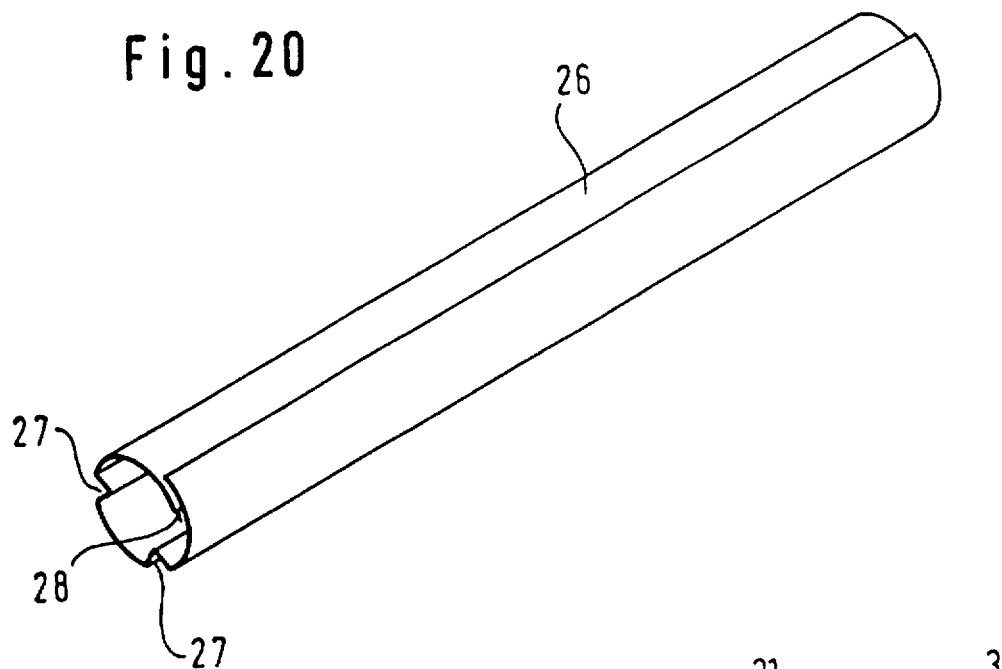
Figure 21:
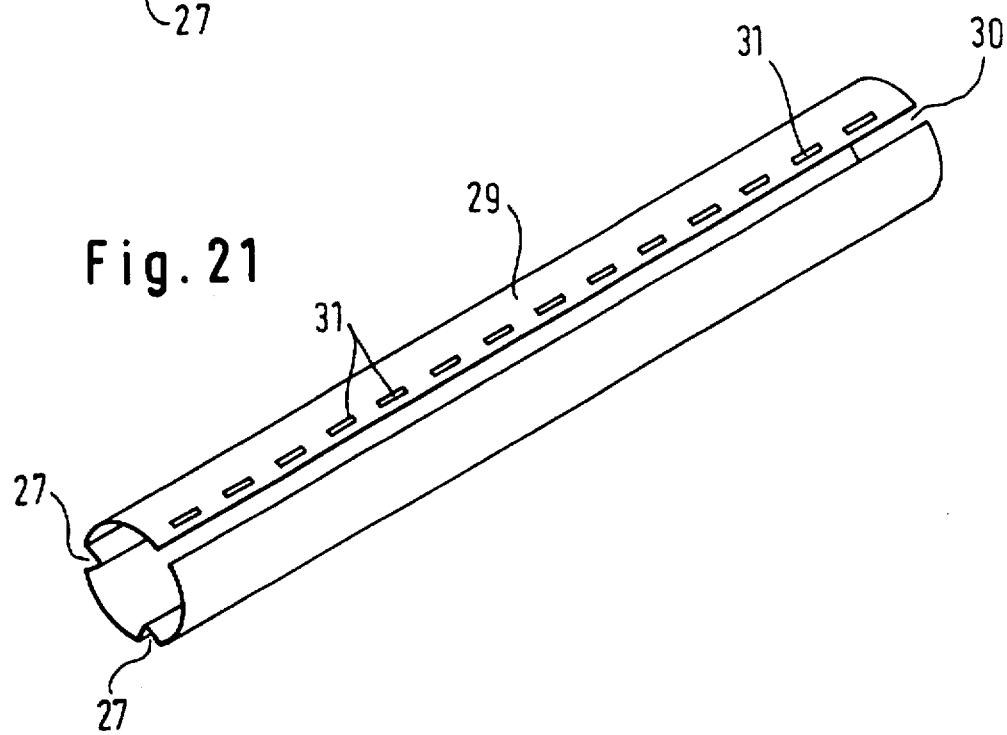

FIG. 11 clarifies the removal of the balloon rod from the finished vascular prosthesis;

FIG. 12 shows an embodiment of the balloon rod in inclined view when folded together;

FIG. 13 shows the balloon rod in accordance with FIG. 12 in the inflated stated, in inclined view;

FIG. 14 shows the fibro-elastic tube in the relaxed state before it is positioned on a guide means in inclined view;

FIG. 15 shows the fibro-elastic tube as in FIG. 14, positioned on a guide tube in inclined view;

FIG. 16 shows the introduction of the replacement vessel in the guide tube which has been covered with the fibro-elastic tube;

FIG. 17 shows the expansion of the replacement blood vessel in the fibro-elastic tube after removal of the guide tube in inclined view;

FIG. 18 shows the winding of the replacement blood vessel in a film which serves as the guide means in inclined view;

FIG. 19 clarifies the fibro-elastic tube, drawn over a film which has been rolled to form a tubular guide means, in inclined view;

FIG. 20 shows another embodiment of the film which has been rolled to serve as the guide means in inclined view; and FIG. 21 shows a further embodiment of a guide tube.

In the embodiment of the inventive vascular prosthesis which is shown in FIGS. 1 to 4, a fibro-elastic tube 2 which is formed of interwoven threads 1 is drawn over a section of a replacement blood vessel 3 taken from a human or animal body. At their intersection points, the fibro-elastic threads 1 have a diameter which is reduced by about 50%, as is shown in FIG. 3. This can be achieved by electro-polishing in the braided state and it has the advantage that even in the case of constant movement of the threads in relation to each other there is almost no abrasion and the danger of the appearance of fatigue fractures of the threads is greatly reduced. The fibro-elastic tube is extended on the replacement vessel 3 at points in the longitudinal direction with an alteration of the diameter and reciprocal displacement of its fibro-elastic threads 1, or it is compressed and thereby it is caused to contact evenly and over the entire area the irregular periphery of the replacement vessel and it is bonded to the replacement vessel as well. The adhesive forms an adhesive layer 4, which is located between the replacement vessel 3 and the fibro-elastic tube as well as in the intermediate spaces between the threads 1 of the fibro-elastic rube. This adhesive in the cured state is so elastic that the fibro-elastic threads 1 of the fibro-elastic tube 2 can be displaced against each other, so that the fibro-elastic tube can also be compressed or extended in the finished prosthesis to a certain extent, whereby bending of the prosthesis is ensured without the danger of kinking under axial load. Apart from an adhesion over the entire area, an only pointwise adhesion between the fibro-elastic tube and the replacement vessel is also possible.

Figure 5:
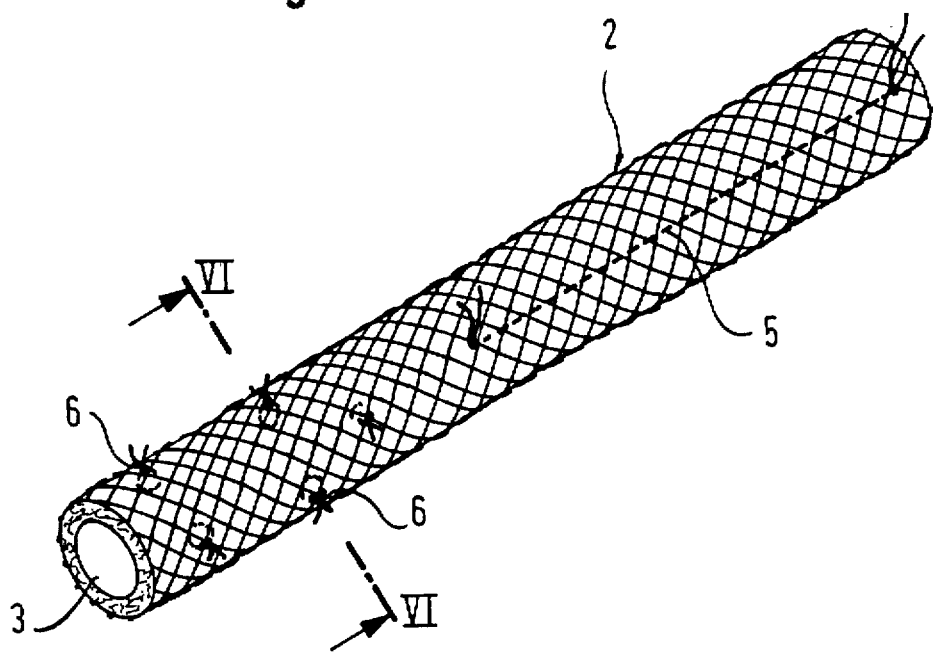
FIG. 5 shows a second embodiment of the vascular prosthesis in accordance with the invention in inclined view.
Figure 6:
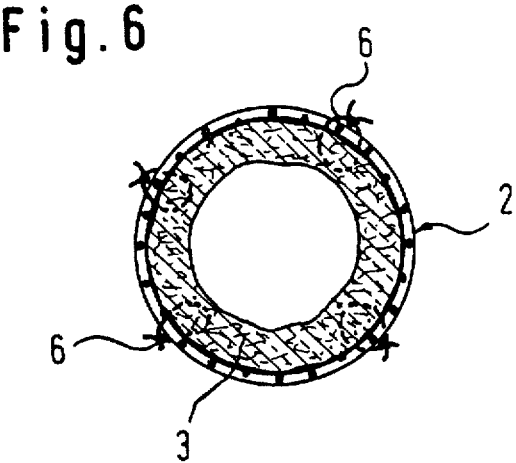
FIG. 6 is a cross-section through the vascular prosthesis along the line VI—VI in FIG. 5.

In the case of the embodiment which is shown in FIGS. 4 and 6 of the inventive prosthesis, the fibro-elastic tube 2 is not connected with the replacement vessel 3 by adhesion, but by seams 5, 6. The seams can be continuous seams 5 or individual button-hole seams 6.

FIGS. 7 to 11 show individual process steps in the production of the vascular prostheses which are shown in FIGS. 1 to 6, in which, for example, as the replacement vessel 3, a section of a vein taken from a human or animal body is used. Initially, as is shown in FIGS. 7 and 8, in the replacement vessel 3, e.g. because of the vein valves, a balloon rod 9 is inserted from the distal end of the vessel and is secured at its front end with a ligature 10 on the replacement vessel 3. Then, in the case of the embodiment which is described here, the surface of the replacement vessel is provided with an adhesive, which can be applied by dabbing and/or by spraying. The lateral branches 8 of the replacement vessel can remain unbound (FIGS. 7 and 8).

The fibro-elastic tube 2 (FIG. 9) which is drawn on to a guide tube 11 by the guide funnel 12 which is arranged or formed on its front end is then moved by means of this guide tube on to the prepared replacement vessel 3, and in fact expediently in the direction from the proximal to the distal end of replacement vessel 3 (FIG. 10). The guide tube has in this case approximately the same length as the replacement vessel 3. Then the guide funnel 12 is cut from the front end of the guide tube 11 and is drawn off over the distal end of the vessel, whereas the guide tube 11 is drawn off over the proximal end of the vessel from the fibro-elastic tube 2 and thereby it is removed from the vessel 3. The fibro-elastic tube 2 which surrounds the replacement vessel 3 can be displaced at points in the longitudinal direction on the vessel and can be expanded or contracted with alteration of the diameter. Thereby it can be adapted with its diameter to the varying periphery of the replacement vessel and can be caused to contact the replacement vessel over its total area and over its entire length.

Then, in the case of the example of the process which is described here, adhesive is applied by dabbing or spraying on to the surface of the fibro-elastic tube 2 and through its mesh and by inflation of the balloon rod 9, the replacement vessel 3 is pressed with its outer periphery on to the fibro-elastic tube. This can be done by connecting the balloon rod to a compressed air lead or by means of a piston guided in a cylinder, for example a syringe with cannula. The pressure can be exerted as long as is necessary to achieve a firm adhesive connection between the replacement vessel 3 and the fibro-elastic tube 2.

After the completion of this adhesion, the balloon rod 9 is emptied, the end of the replacement vessel 3 which is connected with the ligature 10 is cut off and the balloon rod 9 is optionally removed after previous cutting of the other end of the replacement vessel and the fibro-elastic tube 2 in the direction of the arrow (FIG. 11). The vascular prosthesis is now present in the completed form shown in FIG. 1 and it can be used for implantation.

FIGS. 12 to 21 show further embodiments of the ancillary means for the production of the vascular prosthesis in accordance with the invention.

The balloon rod 9 can be made of extensible material and can be expanded by extension by the introduction of a gaseous or liquid pressure agent. FIGS. 12 and 13 show an embodiment of balloon rod 9, in which the balloon consists of a substantially inextensible material. This balloon rod can be folded together in the empty state (FIG. 12), whereas in the state after filling with pressure agent it assumes approximately a sausage shape. FIG. 13 also shows the introduction of the pressure agent into the balloon rod by means of a medical syringe 14 with cannula 15. The balloon rod may also have a conical form in the inflated state instead of a cylindrical form (sausage shape), if this is expedient because of the replacement vessel which is used.

As mentioned above, the expansion of the replacement vessel for the purpose of good adhesion with the fibro-elastic tube 2 which is placed over it can also be done without balloon rod 9 by direct introduction of a liquid or gaseous pressure agent in the replacement vessel. This can be done from the distal end of the replacement vessel, while the proximal end is bound. For this purpose, a cannula 16 can be bound in the distal end by means of a thread 17.

The filling of the balloon rod can in every case be done by using an overpressure valve.

In the case of the embodiment which is shown in FIG. 15, the the guide tube 11 which serves to draw the fibro-elastic tube 2 over the replacement vessel 3 has a lesser length than the replacement vessel in the relaxed state (FIG. 14). This reduces the danger that the replacement vessel which is frequently humid for reasons of preparation will stick to the wall when being positioned over the guide tube. Because the fibro-elastic tube 2 should have a length which corresponds to about the length of the replacement vessel (FIG. 14), in the relaxed, i.e. in the unextended and uncontracted state, the fibro-elastic tube must in this case be contracted before or during its positioning on the guide tube 11 to the length of this tube in the direction of the arrow (FIG. 14). The contracted state of the fibro-elastic tube 2 on the guide tube 11 is maintained by the guide funnel 12 and by the ring 13, which project radially over the periphery of the tube and in this example can be positioned on tube 11.

The insertion of the replacement vessel 3 in the guide tube 11 with the fibro-elastic tube 2 positioned on it can be facilitated by attaching the yarn 18 of ligature 10 of the proximal end of the replacement vessel to the end 19 of a thread catcher rod 20, which has previously been inserted into the guide tube 11 (FIG. 16). By withdrawing the thread catcher rod 20 from the guide tube, the replacement vessel 3 can be drawn into the guide tube. Then the withdrawal of guide tube 11 from the fibro-elastic tube 2 can take place with the removal of the guide funnel 12 or of the ring 13, whereupon the contracted fibro-elastic tube 2 is again relaxed to its original length.

The outer diameter of the vascular prosthesis can be determined before the adhesion process by the application of two semi-circular shells 21 of biocompatible material, between which the replacement vessel covered with the fibro-elastic tube can be inserted (FIG. 17).

The positioning of the fibro-elastic tube over the replacement vessel 3 can also be performed by means of a thin film 22 (FIG. 18). The film can be made of a biocompatible material, such as plastic or metal, and preferably it should have a thickness of 0.1 to 0.4 mm. Expediently it has a pre-rolled from, whereby after the insertion of the replacement vessel in the film it winds itself around the replacement vessel.

FIG. 19 shows an example of an embodiment in which the fibro-elastic tube 2 is drawn over a rolled film 23, which like the film 22 serves as the guide means when drawing the fibro-elastic tube over the replacement vessel 3. In this embodiment, the ends 24, 25 of the rolled film which project over the ends of the fibro-elastic tube 2 are funnel-shaped and/or piston-shaped. This can serve to keep the fibro-elastic tube in a contracted state, whereas the expanded end 24 in funnel form of the rolled film 23 can also be used for easier displacement over the replacement vessel. The funnel-shaped and/or piston-shaped expansion of the ends of the rolled film can be done after the positioning of the fibro-elastic tube, e.g. by thermal deformation.

FIG. 20 shows a rolled film 26 as the tubular guide means for drawing the fibro-elastic tube over the replacement vessel, wihch is provided with longitudinal ribs 27 projecting radially inwards, which are used as the longitudinal guide for the vessel when it is moved over the replacement vessel and therefore they prevent the twisting of the vessel. Moreover the inner longitudinal edge 28 of the rolled film 26 can be used for the same purpose.

FIG. 21 shows an embodiment of guide means 29, which consists of a tube having thin walls with a longitudinal slot 30 extending over its entire length and which is equipped with perforations 31 in its wall. This guide tube which also consists of a metal or plastic is provided with longitudinal ribs 27 which project inwards. The perforations 31, which preferably have a magnitude of 0.5×5 mm, have the purpose of preventing the replacement vessel from sticking to the guide tube when it is being moved over the replacement vessel. The longitudinal slot in the guide tube can also be used as a guide and alignment means for the replacement vessel when it is inducted into the tube, to prevent its twisting. However, the guide tube can also be provided without the longitudinal slot 30.

What is claimed is:

1. A method of forming a vascular prosthesis, the method comprising the steps of:

providing a section of replacement vessel taken from a human or animal body, said replacement vessel having an outer diameter that varies along the length of the vessel; and encasing said vessel-section in a tube having a diameter that is adjustable at substantially each point along a longitudinal axis of the tube, said adjustment in diameter being accomplished by selective longitudinal extension or compression of said tube at points at which said adjustment is made, said encasing step being performed so that the diameter of said tube is adjusted so as to vary along the length of said tube to adapt the diameter of said tube to the varying outer diameter of said vessel-section.

2. A method as in claim 1, further comprising the steps of:

applying an adhesive on at least one of said vessel-section and said tube;

after said encasing and applying steps, pressing an external surface of said vessel-section against said tube by application of internal pressure to said vessel-section; and maintaining said internal pressure until said adhesive is cured.

3. A method as in claim 2, wherein said applying step comprises at least one of dabbing and spraying said adhesive 4. A method as in claim 2, wherein said applying step is performed before said encasing step.

5. A method as in claim 2, wherein said applying step is performed after said encasing step.

6. A method as in claim 2, wherein said internal pressure is applied by introducing a gas or liquid into said vessel-section, and further comprising the step of removing said gas or liquid from said vessel-section after said adhesive is cured.

7. A method as in claim 2, wherein said pressing step includes:

inserting an expansible balloon rod into said vessel-section;

filling said balloon rod with a liquid or gaseous pressure agent;

maintaining said liquid or gaseous pressure agent in said balloon rod until said adhesive is cured;

removing said liquid or gaseous pressure agent from said balloon rod after said adhesive is cured; and withdrawing said balloon rod from said vessel-section after said removal of said liquid or gaseous pressure agent.

8. A method as in claim 7, further comprising the step of securing said vessel-section on said inserted balloon rod.

9. A method as in claim 8, wherein said vessel-section is secured on said inserted balloon rod by ligature.

10. A method as in claim 1, wherein said encasing step includes:

positioning a tubular guide means within said fibro-elastic tube;

positioning said vessel-section within said guide means so that said guide means is located between said vessel-section and said fibro-elastic tube; and withdrawing said guide means from between said vessel-section and said fibro-elastic tube.

11. A method as in claim 1, wherein said encasing step includes:

winding said vessel-section in a film;

covering said film with said fibro-elastic tube; and withdrawing said film from between said vessel-section and said fibro-elastic tube while securing said fibro-elastic tube with respect to said vessel-section.

12. A method as in claim 1, wherein said encasing step includes:

inserting said vessel-section in a longitudinally-slotted, elastically-expansible guide tube;

covering said guide tube with said fibro-elastic tube; and withdrawing said guide tube from between said vessel-section and said fibro-elastic tube while securing said fibro-elastic tube with respect to said vessel-section.

13. A method according to claim 1, wherein said tube is a fibro-elastic tube formed of intersecting threads wound in spiral form around a longitudinal axis of the tube.

14. A method of providing a vascular prosthesis, comprising the steps of:

providing a section of replacement vessel taken from a human or animal body;

encasing said vessel-section in a tube having a diameter that is adjustable at substantially each point along the longitudinal axis of the tube, said adjustment in diameter being accomplished by selective longitudinal extension or compression of said tube at points at which said adjustment is made, said encasing step being performed so that the diameter of said tube is adjusted so as to vary along the length of said tube to adapt the diameter of said tube to the varying outer diameter of said vessel-section; and implanting in the human or animal body said vessel-section encased in said tube.

* * * * *